(12) United States Patent
Empie et al.

(10) Patent No.: US 6,900,240 B2
(45) Date of Patent: *May 31, 2005

(54) METHOD OF PREPARING AND USING COMPOSITIONS EXTRACTED FROM VEGETABLE MATTER FOR THE TREATMENT OF CANCER

(75) Inventors: Mark Empie, Forsyth, IL (US); Eric Gugger, Latham, IL (US)

(73) Assignee: Archer-Daniels-Midland Company, Decatur, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/137,490

(22) Filed: May 1, 2002

(65) Prior Publication Data

US 2003/0003168 A1 Jan. 2, 2003

Related U.S. Application Data

(62) Division of application No. 09/616,150, filed on Jul. 13, 2000, now Pat. No. 6,395,279, which is a division of application No. 09/162,038, filed on Sep. 28, 1998, now Pat. No. 6,261,565, which is a continuation-in-part of application No. 09/035,588, filed on Mar. 5, 1998, now Pat. No. 6,033, 714, which is a continuation-in-part of application No. 08/868,629, filed on Jun. 4, 1997, now Pat. No. 5,792,503, which is a division of application No. 08/614,545, filed on Mar. 13, 1996, now Pat. No. 5,702,752.
(60) Provisional application No. 60/060,549, filed on Oct. 2, 1997.

(51) Int. Cl.[7] .......................... A61K 35/84; A01N 65/00
(52) U.S. Cl. .......................... 514/456; 514/27; 514/783; 536/8; 536/127; 426/634; 426/46; 530/378; 424/757; 424/401; 435/68.1
(58) Field of Search .......................... 514/456, 27, 783, 514/26, 25, 568, 717, 726; 536/8, 127; 426/634, 46; 530/378; 424/757, 401, 195.1; 435/68.1

(56) References Cited

U.S. PATENT DOCUMENTS

| | | |
|---|---|---|
| 3,391,001 A | 7/1968 | Sair |
| 3,461,205 A | 8/1969 | Mansfield et al. |
| 3,780,182 A | 12/1973 | Johnson et al. |
| 3,870,805 A | 3/1975 | Hayes et al. |
| 4,064,277 A | 12/1977 | Yokotsuka et al. |
| 4,157,984 A | 6/1979 | Zilliken |
| 4,166,861 A | 9/1979 | Bonati et al. |
| 4,232,122 A | 11/1980 | Zilliken |
| 4,259,358 A | 3/1981 | Duthie |
| 4,264,509 A | 4/1981 | Zilliken |
| 4,350,688 A | 9/1982 | Schmittmann |
| 4,366,082 A | 12/1982 | Zilliken |
| 4,366,248 A | 12/1982 | Zilliken |
| 4,390,559 A | 6/1983 | Zilliken |
| 4,428,876 A | 1/1984 | Iwamura |
| 4,524,067 A | 6/1985 | Arichi et al. |
| 4,557,927 A | 12/1985 | Miyake et al. |
| 4,883,788 A | 11/1989 | Day et al. |
| 4,889,921 A | 12/1989 | Diosady et al. |
| 4,902,673 A | 2/1990 | Hayakawa et al. |
| 5,032,580 A | 7/1991 | Watanabe et al. |
| 5,141,746 A | 8/1992 | Fleury et al. |
| 5,204,369 A | 4/1993 | Vallee et al. |
| 5,320,949 A | 6/1994 | Shen |
| 5,352,384 A | 10/1994 | Shen |
| 5,424,331 A | 6/1995 | Shlyankevich |
| 5,486,631 A | 1/1996 | Mitchnick et al. |
| 5,506,211 A | 4/1996 | Barnes et al. |
| 5,554,519 A | 9/1996 | Weber et al. |
| 5,554,645 A | 9/1996 | Romanczyk, Jr. et al. |
| 5,637,561 A | 6/1997 | Shen et al. |
| 5,637,562 A | 6/1997 | Shen et al. |
| 5,679,806 A | 10/1997 | Zheng et al. |
| 5,702,752 A | 12/1997 | Gugger et al. |
| 5,763,389 A | 6/1998 | Shen et al. |
| 5,792,503 A | 8/1998 | Gugger et al. |
| 5,830,887 A | 11/1998 | Kelly |
| 5,886,028 A | 3/1999 | Vallee et al. |
| 5,904,924 A | 5/1999 | Gaynor et al. |
| 5,952,374 A | 9/1999 | Clarkson, Jr. et al. ...... 514/456 |
| 6,033,714 A | 3/2000 | Gugger et al. |
| 6,045,819 A | 4/2000 | Takebe |
| 6,051,234 A | 4/2000 | Kataoka et al. |
| 6,171,638 B1 | 1/2001 | Gugger et al. |

(Continued)

FOREIGN PATENT DOCUMENTS

| | | |
|---|---|---|
| CN | 1080863 | 1/1994 |
| CN | 1080864 | 1/1994 |

(Continued)

OTHER PUBLICATIONS

Naik et al., "An in vitro and in vivo study of antitumor effects of Genistein on hormone refractory prostate cancer." Anticancer Research, 14:2617–2620 (1994).

(Continued)

*Primary Examiner*—James O. Wilson
*Assistant Examiner*—Devesh Khare
(74) *Attorney, Agent, or Firm*—Sterne, Kessler Goldstein & Fox PLLC

(57) ABSTRACT

A composition is prepared by extracting and isolating phytochemical fractions from plant matter for treatment of cancer and especially for breast, prostate, skin, colon, urinary and bladder cancer. The composition is enriched preferably with two or more different phytochemical fractions, namely, isoflavones, lignans, saponins and saponogenins, catechins, and phenolic acids. The two selected fractions are different from each other and are combined specifically to form a composition to treat cancer. Soy is the preferred source of these phytochemicals; however, other plants may also be used, such as wheat, psyllium, rice, oats, red clover, kudzu, alfalfa, flax, and cocoa. The composition may be delivered in an easy to use or consume form, such as creams, pills, tablets, capsules, dry powder, health bars, food ingredients and supplements, tablets, soft gels, and the like.

33 Claims, No Drawings

U.S. PATENT DOCUMENTS

| | | | |
|---|---|---|---|
| 6,251,420 B1 | 6/2001 | Miljkovic | |
| 6,261,565 B1 | 7/2001 | Empie et al. | 424/195.1 |
| 6,280,777 B1 | 8/2001 | Bombardelli et al. | |
| 6,303,161 B1 | 10/2001 | Takebe et al. | |
| 6,319,308 B1 | 11/2001 | McComas | |
| 6,391,309 B1 | 5/2002 | Empie et al. | |
| 6,391,310 B1 | 5/2002 | Empie et al. | |
| 6,395,279 B1 * | 5/2002 | Empie et al. | |
| 6,399,072 B1 | 6/2002 | Empie et al. | |
| 6,479,054 B1 | 11/2002 | Fujikawa et al. | |
| 6,482,448 B2 | 11/2002 | Tabor | |
| 6,509,381 B2 * | 1/2003 | Empie et al. | 514/783 |
| 6,517,831 B2 | 2/2003 | Takebe et al. | |
| 6,518,319 B1 | 2/2003 | Empie et al. | |
| 6,607,757 B2 | 8/2003 | Bombardelli et al. | |

FOREIGN PATENT DOCUMENTS

| | | |
|---|---|---|
| EP | 0 348 781 A2 | 6/1989 |
| EP | 0 657 169 A1 | 6/1995 |
| EP | 0 659 402 A2 | 6/1995 |
| EP | 0 795 553 A1 | 9/1997 |
| GB | 831306 | 3/1960 |
| JP | 59-85265 A | 5/1984 |
| JP | 61-30593 A | 2/1986 |
| JP | 61-100524 A | 5/1986 |
| JP | 62-10018 A | 1/1987 |
| JP | HEI 01-312965 | 12/1989 |
| JP | 2-188598 A | 7/1990 |
| JP | HEI 02-261365 | 10/1990 |
| JP | HEI 04-152845 | 5/1992 |
| JP | HEI 04-506402 | 11/1992 |
| JP | HEI 07-147903 | 6/1995 |
| JP | HEI 08-73369 | 3/1996 |
| JP | HEI 10-179100 | 7/1998 |
| JP | HEI 11-12172 | 1/1999 |
| WO | WO 93/23069 | 11/1993 |
| WO | WO-9323069 | 11/1993 |
| WO | WO 95/03816 | 2/1995 |
| WO | WO 95/10512 | 4/1995 |
| WO | WO 97/07811 | 3/1997 |
| WO | WO 97/32593 | 9/1997 |
| WO | WO 98/03084 | 1/1998 |
| WO | WO 99/06057 | 2/1999 |
| WO | WO-9958124 | 11/1999 |

OTHER PUBLICATIONS

Messina et al., "Soy intake and cancer risk: A review of the in vitro and in vivo data." Nutrition and cancer, 21(2), 113–31, 1994.

Barnes et al. "Rationale for the use of genistein–containing soy matrices in chemoprevention trials for breast and prostate cancer." J. Cellular Biochem, Supp. 22:181–187, 1995.

Coward et al. "Genistein, Daidzein, and their B–glycoside conjugates: Antitumor isoflavones in soybean foods from american and asian diets. " J. Agric. Food Chem., 41, 1961–1967, 1993.

Article: No. XP–002096529 "Saponins as Anticarcinogens", "The Journal of Nutrition", by Rao, A. V. and Sung, M. K.

English translation of relevant material re Patent Appln. Laid Open Nos. (1) Hei 02–261365; (2) Hei 01–312965; (3) Hei 04–152845; (4) Hei 08–73369; (5) Hei 07–147903; (6) Hei 04–506402; (7) Hei 10–179100; and (8) Hei 11–12172.

Article: No. XP–002096530 "Dietary Soybean Protein Prevents Bone Loss in an Ovariectomized Rat Model of Osteoporosis", "The Journal of Nutrition", Arjmandi, B. H. et al.

European Patent Office, Patent Abstract of Japan Publication No. 07304655 dated Nov. 21, 1995 for JP 59085265.

Abstract of Japanese Publication No. 07304655 dated Nov. 21, 1995 for JP 4283518.

Abstract of Japanese Publication No. 07304655 dated Nov. 21, 1995 for JP 61100524.

Abstract of Japanese Publication No. 07304655 dated Nov. 21, 1995 for JP 07304655.

Ansel, H.C., et al., "Pharamceutic Ingredients," in *Pharmaceutical Dosage Forms and Drug Delivery Systems*, Ansel, H.C., et al., eds., Williams & Wilkins, Baltimore, MD, pp. 110–116 (1994).

Austin, C.A., et al., Site–specific DNA cleavage by mammalian DNA topoisomerase II induced by novel flavone and catechin derivatives, *Biochem J.* 282:883–889, Portland Press On Behalf Of The Biochemical Society (1992).

Hostettmann, K., and Marston, A., "Triterpene saponin— pharmacological and biological properties," and "Steroid saponin and steroid alkaloid saponin: pharmacological and biological properties," in *Saponins*, Hostettmann, K., and Marston, A., eds., Cambridge University Press, Cambridge, MA, pp. 232–306 (1994).

Hutabarat, L.S., et al., "Isoflavones and Coumestrol in Soybeans and Soybean Products from Australia and Indonesia," *J. Food Comp. Anal.* 14:43–58, Academic Press (Dec. 2001).

Kashiwada, Y., et al., "Tannins as Potent Inhibitors of DNA Topoisomerase II in vitro," *J. Pharm. Sci* 82:487–492, American Pharmaceutical Association (1993).

Kolar, C.W., et al., "Isolated Soy Protein. I. Introduction," and "II. History," in *New Protein Foods. vol. 5 Seed Storage Proteins*, Altschul, A.M., and Wilcke, H.L., eds., Academic Press, Inc., Orlando, FL, pp. 259–261 (1985).

Kudou, S., et al., "Malonyl Isoflavone Glycosides in Soybean Seeds (*Glycine max* Merrill)," *Agric. Biol. Chem.* 55:2227–2233, Japan Society for bioscience, Biotechnology, and Agrochemistry (1991).

Matsuura, M., and Obata, A., "β–Glucosidases from Soybeans Hydrolyze Daidzin and Genistin," *J. Food. Sci.* 58:144–147, Institute of Food Technologists (1993).

Naim, M., et al., "Soybean Isoflavones. Characterization, Determination, and Antifungal Activity," *J. Agr. Food Chem.* 22:806–810, American Chemical Society (1974).

Vennat, B., et al., "Comparative study of water–soluble extracts of herb bennet, strawberry and tormentil," *Boll. Chim. Farmaceutico* 135:355–362, Societa Editoriale Farmaceutica (Jun. 1996).

Walter, E.D., "Genistin (an Isoflavone Glucoside) and its Aglucone, Genistein, from Soybeans," *J. Am. Chem. Soc.* 63:3273–3276, American Chemical Society (1941).

Walz, E., "Isoflavon– und Saponin–Glucoside in Soja hispida," *Justus Liebigs Ann. Chem.* 489:118–155, Verlag Chemie (1931).

English language translation of Walz, E., "Isoflavon– und Saponin–Glucoside in Soja hispida," *Justus Liebigs Ann. Chem.* 489:118–155, Verlag Chemie (1931).

Dialog File 351, English language abstract for Japanese Patent Publication No. JP 59–85265 A, Thomson Derwent (1984).

Dialog File 351, English language abstract for Japanese Patent Publication No. JP 61–30593 A, Thomson Derwent (1986).

Dialog File 351, English language abstract for Japanese Patent Publication No. JP 61–100524 A, Thomson Derwent (1986).

Dialog File 351, English language abstract for Japanese Patent Publication No. JP 62–10018 A, Thomson Derwent (1987).

Dialog File 351, English language abstract for Japanese Patent Publication No. JP 2–188598 A, Thomson Derwent (1990).

* cited by examiner

METHOD OF PREPARING AND USING COMPOSITIONS EXTRACTED FROM VEGETABLE MATTER FOR THE TREATMENT OF CANCER

This is a division of Ser. No. 09/616,150, filed Jul. 13, 2000, now U.S. Pat. No. 6,395,279 which, in turn, is a division of Ser. No. 09/162,038, filed Sep. 28, 1998 (a formal application which replaced provisional application Ser. No. 60/060,549 filed Oct. 2, 1997), now U.S. Pat. No. 6,261,565, which, in turn, is a continuation-in-part of Ser. No. 09/035,588 filed Mar. 5, 1998, now U.S. Pat. No. 6,033,714, which, in turn, is a continuation-in-part of Ser. No. 08/868,629, filed June 4, 1997, now U.S. Pat. No. 5,792,503, which, in turn, is a division of Ser. No. 08/614,545, filed Mar. 13, 1996, now U.S. Pat. No. 5,702,752.

This invention relates to compositions extracted from vegetable matter and more particularly to phytochemicals, including saponogenins and saponins, catechins, lignans, phenolic acids, and isoflavones, and especially those extracted from a family of plants including soy, flax, tea, and cocoa, and methods of using these compositions as nutritional supplements or food additives for treating neurological conditions.

As used herein, the term "isoflavone" includes malonyl, acetyl, glucoside, and aglycone forms of the isoflavones.

BACKGROUND

Currently, there is almost an epidemic of cancer; at least some of which is thought to be either caused or exacerbated by foods having a hormonal supplement derived from an animal origin. This is thought especially true for breast and prostate cancer. Other forms of cancers which are of special concern are skin cancer, colon cancer, urinary cancer, cancer of the bladder and the like.

It is thought that many of those cancers, especially breast and prostate cancers, are either preventable or treatable by a use of phytochemical fractions, especially isoflavones, as a source of supplemental hormones, and particularly if such use begins before a female reaches puberty. For males, apparently the treatments may begin at any time.

However, it is also thought that there are superior results when a plurality of such phytochemical fractions are consumed in combinations which are tailored to have a profile to treat or prevent such cancers. A proper diet should contain the desired phytochemical fractions. Many people do not have or do not like the kind of proper diet which provides the desirable effects. Hence, the challenge is to furnish the necessary phytochemical fractions in a form which is more acceptable. This is achieved in the present invention by a refining process which enables extraction, refining, isolation, and selection of specific phytochemical fractions which are combined and tailored to the needs of specific illnesses, particularly cancers.

Another object of this invention is to provide an optimized extract composition of phytochemical fractions which are present in sufficient concentration to be delivered at the proper dosage in an easy to consume form such as a pill, tablet, capsule, liquid or ingredient in a food including health bars.

This extract may be used alone or combined with one or more other plant extracts to produce the optimized composition. Further, this extract composition may be formulated with one or more other dietary nutrients, such as vitamins, minerals, amino acids, etc., to provide a nutritional supplement further optimized for a desired health effect. All of these ingredients may be combined with necessary binders, excipients, preservatives, colors and the like known to those in the industry in order to produce a suitable tablet, capsule, pill, liquid, cream, powder or food ingredient in a food including health bars.

The improved composition is obtained by fractionating a plant source high in isoflavones, lignans and other phytochemicals such as defatted soybean flakes, soy molasses, soy whey, red clover, alfalfa, flax, cocoa, tea, or kudzu root. These may be fractionated alone or in combination with these other plants known to be high in the various isoflavones, lignans, saponins and saponogenins, catechins and phenolic acids. The fractionation results in substantially removing water, carbohydrates, proteins, and lipids from the source material. The fractionation method may be preferably that disclosed in U.S. Pat. Nos. 5,702,752, 6,261,545; 6,017,555; 6,033,714 or 4,428,876, or an extraction using ethyl acetate or n-butanol may be used. U.S. Pat. Nos. 5,702,752; 6,017,555; 6,033,714; 6,261,545 are assigned to the assignee of this invention.

TABLE 1

| | Ingredients of experimental diets (grams) | | | | | |
|---|---|---|---|---|---|---|
| | Diet 1 casein | Diet 2 SPI | Diet 3 Casein/LSPC | Diet 4 SPI/LSPC | Diet 5 Casein/HSPC | Diet 6 SPI/HSP |
| SPI | 0 | 200 | 0 | 200 | 0 | 200 |
| Casein | 200 | 0 | 200 | 0 | 200 | 0 |
| DL-methionine | 3 | 3 | 3 | 3 | 3 | 3 |
| Corn starch | 150 | 150 | 150 | 150 | 150 | 150 |
| Sucrose | 500 | 500 | 500 | 500 | 500 | 500 |
| Cellulose, BW200 | 50 | 50 | 50 | 50 | 50 | 50 |
| Corn oil | 50 | 50 | 50 | 50 | 50 | 50 |
| Mineral Mix. S10011 | 35 | 35 | 35 | 35 | 35 | 35 |
| Vitamin Mix. V10011 | 10 | 10 | 10 | 10 | 10 | 10 |
| Choline Bitartrate | 2 | 2 | 2 | 2 | 2 | 2 |
| Soy phytochemicals | 0 | 0 | 2 | 2 | 10 | 10 |
| Total (g) | 1000 | 1000 | 1002 | 1002 | 1010 | 1010 |
| (isoflavones, mg/kg diet) | 0 | 245 | 341 | 586 | 705 | 950 |

[1]AIN formulation with minor modification by Dr. E. A. Ulman, Research Diets, Inc

TABLE 2

Final body weight, total food intake, total isoflavone intake, and tumor volume

| Treatment   | Body weight    | Food intake grams/m | Total isoflavone | Tumor volume (cm$^3$)  |
|-------------|----------------|---------------------|------------------|------------------------|
| Casein      | 22.4 ± 0.5[1]  | 46.6 ± 3.1          | 0.00 ± 0.00      | 2.32 ± 0.31[2]         |
| SPI         | 23.1 ± 0.7     | 46.2 ± 2.8          | 17.00 ± 6.37     | 2.06 ± 0.32            |
| Casein/LSPC | 21.4 ± 0.7     | 41.2 ± 3.4          | 14.03 ± 14       | 1.88 ± 0.35            |
| SPI/LSPC    | 22.6 ± 0.6     | 50.1 ± 4.7          | 29.36 ± 2.76     | 1.66 ± 0.29*           |
| Casein/HSPC | 22.2 ± 0.7     | 44.8 ± 6.1          | 76.38 ± 10.40    | 1.64 ± 0.22*           |
| SPI/HSPC    | 22.0 ± 0.6     | 47.5 ± 1.7          | 92.53 ± 3.22     | 1.39 ± 0.30**          |

[1]Values are means ± SE. There are no significant differences of food intake or body weight among treatment groups.
[2]Compared with control group, SPI/LSPC. casein/HSPC, and SPI/HSPC had significantly smaller tumor volumes (*:p < 0.04; **:p < 0.005).

TABLE 3

Effects of treatment on apoptotic index (AI, % TUNEL), proliferation index (PI, % PCNA Staining) and angiogenesis (microvessel density)

| Treatment              | AI (% TUNEL)  | PI (% PCNA)  | Microvessel Density |
|------------------------|---------------|--------------|---------------------|
| Control (n = 2)        | 6.07 ± 0.88   | 60.1 ± 1.1   | 12.5 ± 3.8          |
| Casein/HSPC (n = 2)    | 10.75 ± 0.54  | 51.7 ± 1.3   | 9.7 ± 0.7           |
| P value                | <0.02         | <0.01        | >0.05               |

Values are means ± SE.

In summary, preliminary results indicate that soy products inhibit the s.c. growth of LNCaP tumor in SCID mice, possibly via induction of apoptosis, and inhibition of angiogenesis and proliferation.

Isoflavones or lignans can alleviate menopausal-related symptoms such as hot flashes and osteoporosis as well as alleviate symptoms associated with menstruation. This is further believed to be due to their estrogenic activity. It is believed that the improved composition described here will alleviate these symptoms even more effectively.

Also, isoflavones positively affect various cardiovascular-related conditions, including heart disease, cholesterol (saponins also positively affect cholesterol), angiogenesis and other vascular effects. It is believed that the improved composition will produce results for these cardiovascular conditions at least as beneficial as those hitherto known and at a reduced cost.

As explained earlier, isoflavones, lignans, and saponins are known to individually positively affect various neurological and immunological symptoms. It is believed that the improved composition will result in alleviating neurological and immunological symptoms at least as well as those compounds hitherto known and at a reduced cost. Moreover, it would be expected that some synergism would arise out of the combination described herein.

The improved composition may be administered orally, parenterally, for instance, subcutaneously, intravenously, intramuscularly, intraperitoneally, by intranasal instillation or by application of an aerosol spray to mucous membranes, or to the skin by an ointment or a cream.

Administering the improved composition may be done with any suitable carrier, in solid or liquid dosage form such as tablets, capsules, powders, soft gels, solutions, suspensions, emulsions, ointments, or creams. The improved composition may also be administered as a food supplement or as a food ingredient.

The amount of the improved composition administered will vary depending on the person, the mode of administration, and the desired result. An effective amount is expected to be 10 mg to 2000 mg/per dose.

EXAMPLE 2

Tablet Manufacture

The composition provided for in this patent may be used to prepare tablets or other dosage forms. An example of a capsule preparation is provided in Example 2. The hither the concentration of the active component, the easier it is to form a tablet or emulsion. This leads to an added ability to incorporate other dietary nutrients. An example would be to prepare a phytochemical tablet which incorporates calcium and vitamin E as a supplement to maintain bone health and/or reduce post menopausal symptoms such as hot flashes. In an example of this embodiment, a 600 mg dry compression tablet was prepared containing a total of 125 mg of isoflavones concentrate (50 mg isoflavone compound). Included in the tablet formulation was a source of calcium and magnesium.

Dry compression tablets were produced by first blending the following ingredients: 4 kg of the improved composition (39.83% isoflavones), 1.91 kg sorbitol, 0.095 kg magnesium stearate, and 13.11 kg dicalcium phosphate in a 120 quart capacity Hobart mixer. This blend of ingredients was then dry compressed at 1 ton pressure with a Stokes BB2 simple press into tablets having a total weight of 600 mg containing 125.53 mg of the improved composition and therefore 50 mg of total isoflavones.

Alternatively, a photochemical concentrate may be provided in a single dosage form, a skin cream or as a food ingredient added to conventional food in amounts from 10 mg to 2000 mg/per dose, the purpose of which is to exert a positive effect on health and well being. These benefits include: cancer prevention, estrogen and sex hormone related maladies, inhibition of the pituitary-thyroid-gonadotrophic axis, alcohol dependency reduction, modulation of the cardiovascular, immune and nervous systems, antiviral effects and analgesic effects.

EXAMPLE 3

Two-piece gelatin capsules were produced by filling the receiving end of the empty size "0" capsules with 0.106 g of the improved composition (44.35% isoflavones) and closed with the capping end, providing a capsule containing 47.2 mg of total isoflavones.

EXAMPLE 4

A comparison between various sources of phytochemical preparations is given in Table 4. It is readily seen that the phytochemical components of the composition of the "Isoflavone Concentrate" of this invention is substantially higher than the corresponding amounts in the natural vegetable materials. Notably, the amount of glycone isoflavones and saponins are over 100 times more concentrated compared to the food source and over twenty times more concentrated compared to the germ of the plant which naturally concentrates these phytochemicals. Comparison of the "Isoflavone Concentrate" of this invention to other concentrates shows that the isoflavone fraction predominates in these latter products, reducing the amount of other healthful phytochemicals. Additionally, the extraction methods of these other products employ techniques which modify the components, particularly the isoflavones, so that they are not identical to the substances found in the natural vegetable material (U.S. Pat. No. 5,637,562).

One version of the improved composition was compared to other previously described compositions. The results are shown in Table 4.

vone concentration by HPLC. Results are tabulated as shown in Table 5.

TABLE 5

Differential Solubility of Isoflavone Glycosides vs. Aglycones

| Isoflavone sample | Genistein (ppm) | Genistin (ppm) | Daidzein (ppm) | Daidzin (ppm) |
|---|---|---|---|---|
| Genistein | 7.42 | | | |
| Genistin | | 33.89 | | |
| Daidzein | | | 3.64 | |
| Daidzin | | | | 48.51 |
| Isoflavone Concentrate | 0.492 | 30.075 | 0.672 | 37.69 |

The glycoside forms, genistin and daidzin, are at least 4.57 and 13.32 fold higher in concentration at 37° C. than their corresponding aglycone forms, respectively.

TABLE 4

Comparative Products to the Invention

| Product Example | Isoflavone Glycosides in Product (mg/g) | Isoflavone Aglycones in Product (mg/g) | Genistein/ Daidzein Ratio | Lignans (mg/g) | Saponins (mg/g) | Phenolic Acids (mg/g) |
|---|---|---|---|---|---|---|
| Improved composition | 401.0 | 3.37 | 1.06 to 1 | 0.2 | 460.7 | 25.47 |
| Soybean | 1.748–2.776[a] | 0.044[a]–0.075 | 1.59–2.7 | NA | 0.9–3.2[b] | |
| Soy Flour (defatted) | 1.969[a] | 0.045[a] | 3.58 | 0.0013 | | 2.870[c] |
| Soy germ | 24.32[d] | 0.85[d] | | NA | 16.7–1.98[b] | NA |
| Product[e] patent (PTI) | NA | 2.5–6.5[e] | 0.5–3.5 | NA | NA | NA |
| Product[f] patent (PTI) | NA | 5.1–14.7[f] | 0.433–3.48 | NA | NA | NA |
| Product[g] patent (PTI) | NA | 1.7–3.5[g] | 0.66–2.86 | NA | NA | NA |
| PTI product[h] | NA | 970 | 12.8 | NA | NA | NA |
| PTI product[h] | NA | 640 | 2.0 | NA | NA | NA |
| Soy Molasses (dried) | 27.6 | 0.1 | 1.37 | NA | NA | 5.788 |
| Novogen[i] | 0.0 | 550 | 1–1.7 to 1 | NA | NA | NA |

[a]Wang H. and Murphy P. A., J. Agric. Food Chem 1994, 42, 1666–1673.
[b]Anderson R. L. and Wolf W. J, J. Nutr 125:58IS–588S, 1995
[c]Seo A. and Morr C. V., J. Agric Food Chem 1984, 32, 530–533.
[d]Soy Life ™ promotional literature
[e]WO 95/10530, PCT/US94/10697
[f]WO 95/10512, PCT/US94/10699
[g]WO 95/10529, PCT/US94/10696
[h]NCI paper
[i]Novogen promotional literature

EXAMPLE 5

The improved composition, containing the glycoside forms of isoflavones, has as one aspect an improved solubility at body temperature over the previously described compositions containing the aglycoside forms.

Separate solutions (0.02% in distilled water) were made for genistein, genistin, daidzein, daidzin, and isoflavone concentrate in volumetric flasks. Samples were then placed in a 37° C. water bath for 17 hours, followed by rapid filtration through a 0.2 micron syringe-type filter to remove particulates. Filtered samples were then analyzed for isofla- The modifications made to the isoflavones are to remove the carbohydrate attached to the isoflavone moiety. This modification renders the isoflavone less soluble in water. Maintenance of the natural modification, glycosylation, enhances solubility. This fact is shown in the comparative solubility chart of Table 5. This chart shows that the genistin isoflavone is 4.6 times higher and the daidzin isoflavone is 13.3 times higher than the corresponding non-glycosylated form. Higher solubility can lead to better bioavailability to intestinal organisms. The glycosylation does not inhibit absorption in the gut because the intestinal microflora convert the glycone form to the aglycone form before absorption occurs.

EXAMPLE 6

Extraction of Lignans from Flax

Lignans can be readily extracted from flax using this following method.

978 g of defatted flax meal (F1) was extracted with 2000 g of 85% ethanol at 40° C. for 10 minutes, forming a slurry. The resulting slurry was filtered and extraction was repeated twice with a total of 6000 g of ethanol.

The ethanolic fraction was then evaporated under vacuum at 70° C., resulting in an aqueous fraction of 1186 g. The aqueous fraction was combined with 1000 g of water and mixed.

The mixed sample was then ultra-filtered through a 5000 molecular weight cutoff membrane, resulting in a 767 g permeate fraction and a retentate action of 1283 g.

The retentate fraction was freeze-dried, resulting in a 27.84 g sample (F2).

The 767 g permeate fraction at 50° C. was fed to a 35 ml bed volume, XAD-4 resin column at a rate of 10 ml/min. The column effluent was collected and dried, resulting in a 14.8 g sample (F3). XAD-4 is a trademark for an absorbent resin, available from Rohm & Haas.

The column was then eluted with four bed volumes (140 ml) of 70% ethanol at 50° C. The eluent sample was evaporated under vacuum at 70° C. and dried, resulting in a 1.79 g sample (F4). The four fractions were then analyzed for their lignan content, measured as the concentration by weight of secoisolariciresinol. As Table 6 shows, this extraction method enriches lignan concentration.

TABLE 6

LIGNAN CONCENTRATIONS AS SECOISOLARICIRESINOL

| FRACTION | F1 | F2 | F3 | F4 |
|---|---|---|---|---|
| SECO. CONC. (mg/g) PHENOLIC ACID | 2.3 | 1.9 | 4.8 | 13.4 |

While the present invention has been disclosed in terms of the preferred embodiment in order to facilitate a better understanding of the invention, it should be appreciated that the invention can be embodied in various ways without departing from the principles of the invention. Therefore, the invention should be understood to include all possible embodiments, modifications, and equivalents to the described embodiment which do not depart form the principles of the inventions as set out in the appended claims.

What is claimed is:

1. A method of treating a cancer selected from the group consisting of breast cancer, skin cancer, colon cancer, urinary cancer, bladder cancer, or prostate cancer comprising administering to a person an amount therapeutically effective in treating said cancer of a composition comprising at least two phytochemical fractions selected from the group consisting of isoflavones, lignans, saponins, saponogenins, catechins, and phenolic acids, said at least two phytochemical fractions being different from each other, and wherein at least one of the selected phytochemicals comprises at least 10% by weight of the composition.

2. The method of claim 1 wherein said phytochemical fractions are extracted from plant matter selected from the group consisting of soy, wheat, psyllium, rice, oats, red clover, kudzu, flax, alfalfa, tea, and cocoa.

3. The method of claim 2 wherein said treatment is for breast cancer.

4. The method of claim 2 wherein said treatment is for skin cancer.

5. The method of claim 4 wherein said phytochemical fractions are mixed with a carrier selected from a group consisting of skin cream or skin lotion.

6. The method of claim 4 wherein said phytochemical fractions are in a form for topical application.

7. The method of claim 2 wherein said treatment is for colon cancer.

8. The method of claim 2 wherein said treatment is for urinary cancer.

9. The method of claim 2 wherein said treatment is for bladder cancer.

10. The method of claim 2 wherein said treatment is for prostate cancer.

11. The method of claim 2 in which said plant matter is soy.

12. The method of claim 11 in which said soy is selected from the group consisting of soybean, soy foods, soy molasses, soy whey, soy protein, and soy flour.

13. The method of claim 1 wherein said composition is formed into a product for oral delivery comprising between about 10 milligrams and about 2000 milligrams of said composition.

14. The method of claim 1 wherein said composition is formed into a product for oral delivery selected from the group consisting of:
 a predetermined dosage of said composition;
 a gelatin capsule;
 a liquid; and
 a food supplement composition in a concentrated, easy to consume dosage.

15. The method of claim 1 including the further step of forming said composition into a product selected from a group consisting of a concentrate, dried powder, liquid, capsule, pellet, pill, a food supplement, health bar, intranasal, and spray.

16. The method of claim 1 in which said composition is comprised of at least 70% by weight of said phytochemical fractions.

17. The method of claim 1 in which said composition is comprised of at least 80% by weight of said phytochemical fractions.

18. The method of claim 1 in which said composition is comprised of at least 90% by weight of said phytochemical fractions.

19. The method of claim 1 wherein said phytochemical fractions are in the ranges of about 5%–95% isoflavones; 0%–70% lignans; 2%–70% saponins and saponogenins.

20. The method of claim 19 wherein the ratio of saponins plus saponogenins to isoflavones in the composition is in the range of about 1:100 to about 100:1.

21. The method of claim 1 in which the ratio of isoflavones to lignans in the composition is in the range of about 1000:1 to about 1:50.

22. The method of claim 1 wherein said first phytochemical fraction is isoflavones and said second phytochemical fraction is saponins and saponogenins.

23. The method of claim 22 wherein said isoflavone fraction is selected from a group consisting of malonyl, acetyl, glucoside, and aglycone forms.

24. The method of claim 1 further comprising a dietary supplemental nutrient selected from the group consisting of vitamins and minerals.

25. The method of claim 24 wherein said dietary supplemental nutrient is selected from the group consisting of dicalcium phosphate, magnesium stearate, calcium citrate, calcium malate, and other calcium sources.

26. The method of claim 1 wherein said composition is formed into a product for oral delivery selected from the group consisting of tablets, capsules, pills, concentrates, powders, liquids, and added food ingredients.

27. The method of claim 26 wherein said product is a tablet comprising said composition; and a filler selected from the group consisting of sorbitol, lactose, cellulose and dicalcium phosphate.

28. The method of claim 27 wherein said tablet comprises between about 15% and about 25% by weight of said composition and between about 65% and about 85% by weight of said filler.

29. The method of claim 27 wherein said tablet comprises between about 15% and about 25% by weight of said composition;

between about 60% and about 84% by weight of said filler; and between about 1% and about 25% by weight of a dietary supplemental nutrient selected from the group consisting of vitamins and minerals.

30. The method of claim 29 wherein said dietary supplemental nutrient is selected from the group consisting of dicalcium phosphate, magnesium stearate, calcium citrate, calcium malate, and other calcium sources.

31. The method of claim 1 wherein said plant matter is fractionated to substantially isolate individual ones of said phytochemical fractions.

32. The method of claim 1, wherein at least one of the selected phytochemical fractions comprises at least 39.83% by weight of said composition.

33. The method of claim 1, wherein at least one of the selected phytochemical fractions comprises at least 44.35% by weight of said composition.

* * * * *

UNITED STATES PATENT AND TRADEMARK OFFICE
CERTIFICATE OF CORRECTION

PATENT NO. : 6,900,240 B2
APPLICATION NO. : 10/137490
DATED : May 31, 2005
INVENTOR(S) : Empie et al.

It is certified that error appears in the above-identified patent and that said Letters Patent is hereby corrected as shown below:

On the title page item (57), line 14,
Delete "capsules, dry powder" and insert --capsules, pellets, dry powder,-- therefor.

Item (56), page 2, Col. 1, line 1, Under Other Publications: Add --Keung et al. "Therapeutic lessons from Traditional oriental medicine to contemporary occidental pharmacology." Abstract EXS, 71, 371-81, 1994.-- therefor.

Column 2, Table 1, Footnote 1, delete "Inc" and insert --Inc.-- therefor.

Column 4, Line 26, delete "hither" and insert --higher-- therefor.

Column 5, Table 4, Footnote a, delete "Wang II." and insert --Wang, H.J.-- therefor.

Column 5, Table 4, Footnote b, delete "W.J.," and insert --W.J.-- therefor.

Column 5, Table 4, Footnote b, delete "58IS-588S" and insert --581S-588S-- therefor.

Column 7, Line 19, delete "action" and insert --fraction-- therefor.

Column 7, Line 50, delete "form" and insert --from-- therefor.

Signed and Sealed this

Fifteenth Day of April, 2008

JON W. DUDAS
*Director of the United States Patent and Trademark Office*